United States Patent

Clarke et al.

(10) Patent No.: US 9,464,979 B2
(45) Date of Patent: Oct. 11, 2016

(54) MONITORING A CONDUCTIVE FLUID CONDUIT

(71) Applicant: Teledyne Limited, West Drayton (GB)

(72) Inventors: Daniel Clarke, Brighton (GB); Barry John Hemblade, Hove (GB)

(73) Assignee: Teledyne Limited (GB)

( * ) Notice: Subject to any disclaimer, the term of this patent is extended or adjusted under 35 U.S.C. 154(b) by 271 days.

(21) Appl. No.: 14/369,129

(22) PCT Filed: Nov. 23, 2012

(86) PCT No.: PCT/GB2012/000861
§ 371 (c)(1),
(2) Date: Jun. 26, 2014

(87) PCT Pub. No.: WO2013/102746
PCT Pub. Date: Jul. 11, 2013

(65) Prior Publication Data
US 2014/0354307 A1    Dec. 4, 2014

(30) Foreign Application Priority Data

Jan. 6, 2012 (GB) .................................. 1200179.8

(51) Int. Cl.
*G01N 17/04* (2006.01)
*G01N 27/20* (2006.01)

(52) U.S. Cl.
CPC .............. *G01N 17/04* (2013.01); *G01N 27/20* (2013.01)

(58) Field of Classification Search
CPC .... G01N 17/00; G01N 17/006; G01N 17/02; G01N 17/04; G01N 27/04; G01N 27/045; G01N 27/046; G01N 27/20
USPC .......................................................... 324/700
See application file for complete search history.

(56) References Cited

U.S. PATENT DOCUMENTS 4,048,558 A    9/1977 Goodman
4,947,132 A    8/1990 Charoy et al.
(Continued)

*Primary Examiner* — Jermele M Hollington
*Assistant Examiner* — Robert P Alejnikov, Jr.
(74) *Attorney, Agent, or Firm* — Duncan Galloway Egan Greenwald, PLLC; Kevin T. Duncan

(57) ABSTRACT

There is described an apparatus for monitoring a conductive fluid conduit arranged to carry a fluid stream. The apparatus comprises a power supply, a plurality of electrical contact points connected to the fluid conduit, a voltage measurement device, and a processor. The power supply has a reference mode of operation and a sample mode of operation. In the reference mode of operation the power supply is operable to supply an alternating electric current through the fluid conduit at a high frequency such that the current is confined near the surface of the fluid conduit due to the skin effect. In the sample mode of operation the power supply is operable to supply an electric current through a full thickness of the fluid conduit. The voltage measurement device is operable to measure the voltage between pairs of said electrical contact points so as to obtain reference values of electrical resistance of the fluid conduit when the power supply is in the reference mode of operation and so as to obtain sample values of electrical resistance of the fluid conduit when the power supply is in the sample mode of operation. The processor is operable to modify the sample values of electrical resistance based on the corresponding reference values of electrical resistance so as to compensate for temperature variations.

There is also described a corresponding method for monitoring a conductive fluid conduit arranged to carry a fluid stream.

21 Claims, 4 Drawing Sheets

(56) References Cited

U.S. PATENT DOCUMENTS

| | | |
|---|---|---|
| 6,476,624 B1 | 11/2002 | Chuman et al. |
| 6,946,855 B1 * | 9/2005 | Hemblade .............. G01N 17/04 324/700 |
| 7,878,047 B2 * | 2/2011 | Hemblade ............ G01N 29/222 73/61.75 |
| 2007/0250277 A1 | 10/2007 | Hagit et al. |
| 2009/0085585 A1 * | 4/2009 | Lu .......................... G01N 17/04 324/700 |

* cited by examiner

MONITORING A CONDUCTIVE FLUID CONDUIT

FIELD OF THE INVENTION

The present invention relates to an apparatus and method for monitoring a conductive fluid conduit. For example, the present apparatus and method may be used for monitoring oil and gas pipelines.

BACKGROUND OF THE INVENTION

Corrosion sensors are used in the detection and monitoring of loss of material, such as the internal surface of a pipeline wall, due to corrosion and/or erosion from interaction between the material and the environment in contact with the material. Such conditions exist in oil or gas pipelines.

Commonly, corrosion sensors use electrical resistance methods to detect loss of material due to corrosion/erosion. Such sensors are described, for example, in U.S. Pat. No. 6,946,855, U.S. Pat. No. 6,680,619, U.S. Pat. No. 6,680,619, US2011/001498, WO01/70003, WO02/39102, WO2005/036152 and WO8303675.

In U.S. Pat. No. 6,946,855 (Cormon Limited), an apparatus is disclosed for monitoring the effect on a material of exposure to a fluid, and thereby monitoring the effect on a section of pipe for carrying the fluid. The apparatus includes a sensor element exposed to the fluid and formed as a ring of the material coaxially mounted within, but electrically insulated from, the section of pipe. Changes in the electrical resistance of the sensor element are monitored. Preferably, the apparatus also includes a reference element electrically insulated from the pipe, electrically connected in series to the sensor element and protected from exposure to the fluid. The elements may both be made from the same material as the pipe and, as they are contained within it, experience the same temperature and pressure variations as the pipe. In this manner a change in the resistance of the sensor element caused by corrosion/erosion by the fluid accurately indicates the degree of corrosion/erosion of the pipe carrying the fluid.

U.S. Pat. No. 6,680,619 (Corrocean ASA) describes a sensor device for registering voltage drops on corrosion exposed structures. The sensor device is coupled to a surface area of the structure to which a voltage is supplied by electrodes causing an excitation current in that area. There are a plurality sensors arranged in a matrix defining measurement points with defined distances, to obtain signals related to the voltage distribution in the surface area as a basis for determining material thickness and/or structure in the measurement area, thereby determining wall thickness and/or the occurrence of corrosion and/or erosion defects.

US2011/001498 (Roxar Flow Measurement AS) describes a method and device for monitoring a zone of a metal structure in terms of its electrical resistance in order to detect possible defects in the structure, by periodically passing current through the zone in different directions while measuring and recording voltage drops in a number of selected unit areas within the zone, and by combining, for each unit area, at least two measured values recorded during at least two measurements made with current passing in different directions, and by comparing values obtained by at least one similarly obtained value made earlier.

WO01/70003 (British Nuclear Fuels Plc) provides a method and apparatus aimed at improving the range of situations to which field signature method based techniques are applicable from measuring corrosion. In particular, WO01/70003 is directed towards situations in which the location requiring investigation has been the subject of pre-existing corrosion. WO01/70003 provides a method of investigating corrosion at a location, the method including providing a mounting unit for two or more electrical contacts, introducing the mounting unit to a replica of the location which has not corroded, measuring the voltage between the two or more electrical contacts at one or more times, the two or more electrical contacts being in contact with a replica of the location being investigated, introducing the mounting unit to the location which may have corroded, measuring the voltage between and/or the variation in the voltage between two or more electrical contacts at a first time and at one or more other times, the two or more electrical contacts being in contact with the location being investigated, passing a current through the replica location at the time of the voltage measurement and through the location at the time of the voltage measurements. The current is provided by a given source for the various voltage measurements. The voltage measurement for the replica location defines the characteristics for an uncorroded location. The voltage measurements for the location indicates the extent of corrosion which has occurred by the time of the first voltage measurement for the location and/or indicates the progress of corrosion between the first time and one or more of the other times of voltage measurement for the location.

In WO02/39102 (British Nuclear Fuels Plc), a method of monitoring or predicting corrosion using a field signature method is provided which is intended to be applicable to non-linear locations, such as bends, junctions and the like. The method includes obtaining information on a relationship which links voltage measurements, obtained for a location, between two or more electrical contacts in contact with the location at a first time and one or more other times when a current is passed through the location, to the loss of material from the location. The information on the relationship is used in a modelling process which includes the generation of a model of the location, two or more points on that location and modelling the values generated for the voltages which will be measured between the two or more points with a current applied to the location at a first and at least at a second time. The model includes a change in configuration of the location between the first time and the second time so as to model loss of material from the location. The relationship has the expression of a relationship between a factor relating to the model voltage values and a factor relating to the change in configuration and/or location.

In WO2005/036152 (General Electric Company), a system and method for monitoring defects in a structure are provided. The system includes a power supply for supplying an electric current to a monitoring area of the structure and a reference. The system also includes a measurement circuit for measuring a potential drop across at least two contact points of the monitoring area and at least two contact points of the reference. The system also includes a processor adapted to determine a ratio of the monitoring area potential drop to the reference potential drop indicative of a percentage change in a thickness of the structure. The method includes the steps of supplying the current to the monitoring area and the reference; measuring a first potential drop across the monitoring area and the reference; and determining the ratio indicative of the percentage change in the thickness of the structure.

WO83/03675 (Sentralinstitutt For Industriell Forskning) relates to monitoring large structures to detect defects, e.g. cracks. An electric current is impressed on a steel structure equipped with contact points between which are measured voltage drops caused by the impressed current. A relatively large number of fixed contact points are used all over the area which is to be monitored. The voltage drops are measured between selected pairs of contact points and these voltage drops are compared with corresponding voltage drops having been measured previously in the same manner when the structure was in an initial condition, preferably without any defects. Such monitoring is mainly applicable on oil drilling rigs and petroleum production platforms for exploitation of oil and gas fields offshore, where it is important that the monitoring can be performed by means of robust and simple devices resistible to the prevailing rough environments.

The sensitivity of such prior art corrosion detector arrangements is limited by various factors. For instance, changes in the temperature in the environment in which the pipeline is situated affect the electrical resistance of the pipe (e.g. the resistance of steel may change by 0.4% per ° C.). In electrical resistance corrosion monitoring systems configured with an element having an exposed surface to the environment and a reference system external to the environment such as the pipeline fluid environment, changes in fluid temperatures significantly limit the accuracy and sensitivity of the monitoring system if the temperature of the pipeline and external reference system differ. To illustrate, a nominal difference in temperature of 0.25° C. between the pipeline and reference system will cause a change in the resistance ratio of 1000 ppm.

Some prior art systems compensate for temperature variations by taking temperature measurements in the vicinity of the pipeline. However, such temperature measurements will not additionally compensate for hydrostatic and thermal stresses induced in pipeline structures which also influence the measured resistive voltages.

Other prior art systems compensate for temperature by having a sample measurement device (which is affected by both corrosion and temperature) and a separate reference measurement device (which is not affected by corrosion, but is at the same temperature as the sample device). However, in practice, it can be difficult to ensure that the temperature of the reference device exactly matches that of the sample device.

The present invention seeks to provide an improved monitoring system which does not require a separate reference measurement device, but is still able to accurately compensate for temperature and stress variations in electrical resistance.

SUMMARY OF THE INVENTION

According to a first aspect of the present invention, there is provided an apparatus for monitoring a conductive fluid conduit arranged to carry a fluid stream. The apparatus comprises a power supply, a plurality of electrical contact points connected to the fluid conduit, a voltage measurement device, and a processor. The power supply has a reference mode of operation and a sample mode of operation. In the reference mode of operation, the power supply is operable to supply an alternating electric current through the fluid conduit at a high frequency such that the current is confined near the surface of the fluid conduit due to the skin effect. In the sample mode of operation, the power supply is operable to supply an electric current through a full thickness of the fluid conduit. The voltage measurement device is operable to measure the voltage between pairs of said electrical contact points so as to obtain reference values of electrical resistance of the fluid conduit when the power supply is in the reference mode of operation and so as to obtain sample values of electrical resistance of the fluid conduit when the power supply is in the sample mode of operation. The processor is operable to modify the sample values of electrical resistance based on the corresponding reference values of electrical resistance so as to compensate for temperature variations.

Thus, the present apparatus is able to monitor oil or gas pipe wall thickness non-intrusively over an extended area. Furthermore, the present apparatus is able to compensate for temperature variations without the need for a separate reference measurement device. In contrast, the present invention uses the same electrical contact points for both the sample and reference measurements, but a different injection current (i.e. a high frequency injection current to induce skin effects, or an alternative injection current to provide current through the full thickness of the fluid conduit).

Advantageously, the processor is further operable to determine a thickness of the fluid conduit based on the modified sample values of electrical resistance. Wall thickness monitoring is the primary aim of the apparatus of the present invention.

In the sample mode of operation, the power supply may be operable to supply an alternating electric current at a low frequency, or may be operable to supply a direct electric current, so as to provide electric current through a full thickness of the fluid conduit.

Advantageously, the apparatus has a plurality of current injection modes. In each current injection mode the power supply is operable to be connected to the fluid conduit by means of a respective pair of current input/output points. In one advantageous embodiment, the pairs of current input/output points are selected from the plurality of electrical contact points.

Advantageously, the apparatus further comprises an acoustic sensor that is acoustically coupled to the fluid conduit. The acoustic sensor is arranged to provide a signal which varies in dependence upon acoustic noise generated by impacts of particles and fluid in the fluid stream on the fluid conduit. In this embodiment, the apparatus is able to provide a qualitative distinction between metal loss due to corrosion and metal loss due to sand. More advantageously, the processor is further operable to qualitatively indicate an amount of particulate matter in the fluid stream based on the signal provided by the acoustic sensor.

Advantageously, the processor is further operable to determine the corrosion and/or erosion of the fluid conduit based on the modified sample values of electrical resistance.

Optionally, the apparatus further comprises a pressure sensor. Advantageously, the processor is further operable to modify the sample values of electrical resistance based on the sensed pressure so as to compensate for pressure variations.

Optionally, the apparatus further comprises a temperature sensor to provide redundancy.

Advantageously, the electrical contact points are disposed in a plane perpendicular to a flow direction of the fluid stream along the fluid conduit.

Advantageously, the fluid conduit is a section of a pipe having a substantially circular cross-section. Optionally, said electrical contact points comprise at least one pair of diametrically opposed electrical contact points. Optionally, said electrical contact points comprise a predetermined number of pairs of diametrically opposed electrical contact points, said electrical contact points being regularly spaced around the circumference of the section of the pipe. This embodiment enables variations in electrical resistance radially around the pipe to be monitored using the sectors defined by the radial locations of the electrical contact points. Alternatively, the electrical contact points are mainly disposed in a semi-circular half of the section of pipe. This embodiment enables half of the pipe (e.g. the top half or the bottom half) to be preferentially monitored so as to identify local defects.

According to a second aspect of the present invention, there is provided a system comprising a plurality of apparatuses according to the first aspect. The plurality of apparatuses are mutually spaced along the fluid conduit in the flow direction. This aspect enables the mapping of wall thickness over a longitudinal length of pipe.

According to a third aspect of the present invention, there is provided a method for monitoring a conductive fluid conduit arranged to carry a fluid stream. The method comprises the steps of: (a) obtaining reference values of electrical resistance of the fluid conduit by driving an alternating electric current through the fluid conduit at a high frequency such that the current is confined near the surface of the fluid conduit due to the skin effect, and by measuring the voltage between pairs of electrical contact points connected to the fluid conduit; (b) obtaining sample values of electrical resistance of the fluid conduit by driving an electric current through a full thickness of the fluid conduit, and by measuring the voltage between said pairs of electrical contact points; and (c) modifying the sample values of electrical resistance based on the corresponding reference values of electrical resistance so as to compensate for temperature variations.

Advantageously, the method further comprises determining a thickness of the fluid conduit based on the modified sample values of electrical resistance.

The step of obtaining sample values of electrical resistance may comprise driving an alternating electric current at a low frequency through a full thickness of the fluid conduit, or may comprise driving a direct electric current through a full thickness of the fluid conduit.

Advantageously, a measurement cycle comprises the steps of obtaining reference values of electrical resistance and obtaining sample values of electrical resistance for a plurality of current injection modes. In each current injection mode, electric current is driven through the fluid conduit via a respective pair of current input/output points. More advantageously, the pairs of current input/output points are selected from the pairs of electrical contact points.

In one embodiment, the steps of obtaining reference values of electrical resistance and obtaining sample values of electrical resistance are performed successively.

In one embodiment, the step of obtaining reference values of electrical resistance further comprises driving an alternating electric current through the fluid conduit at at least one other high frequency, and measuring the voltage between said pairs of electrical contact points, such that a temperature gradient through the thickness of the fluid conduit may be determined. This embodiment enables account to be taken of a temperature gradient through the pipe wall (e.g. in instances where the external pipe wall is at a different temperature to the internal pipe wall).

Other preferred features of the present invention are set out in the appended claims.

BRIEF DESCRIPTION OF THE DRAWINGS

Embodiments of the present invention will now be described by way of example with reference to the accompanying drawings in which.

DETAILED DESCRIPTION OF A PREFERRED EMBODIMENT

In many ways, the present invention may be considered to be an extension of the corrosion sensor described in U.S. Pat. No. 6,946,855 (Cormon Limited). Therefore, the apparatus of U.S. Pat. No. 6,946,855 will first be described in detail below followed by a description of the modifications which give rise to the present invention.

The Corrosion Sensor of U.S. Pat. No. 6,946,855 (Cormon Limited)

Figure 1:
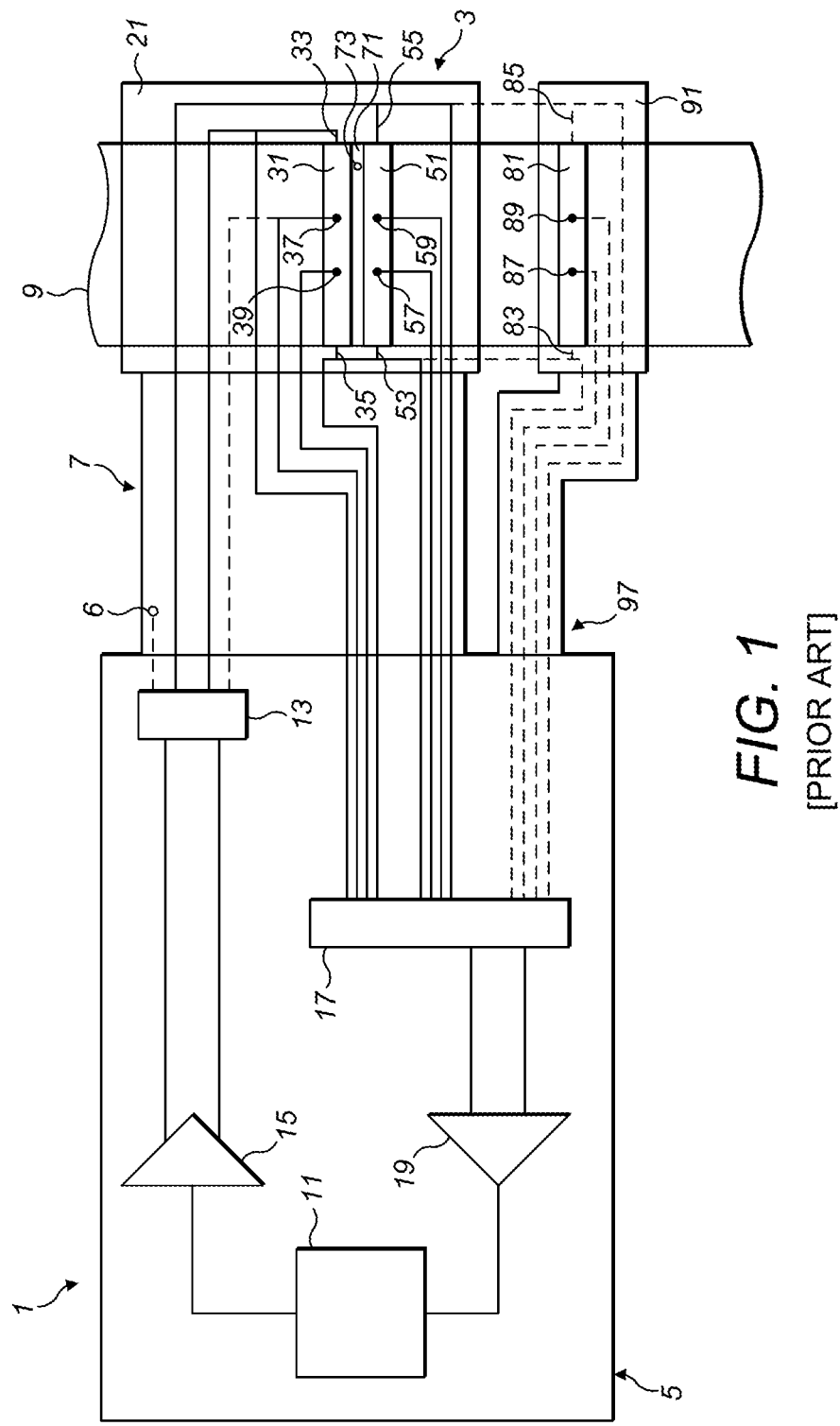
FIG. 1 shows a block circuit diagram of the corrosion sensor of U.S. Pat. No. 6,946,855.

A corrosion sensor 3, which is used in a corrosion monitoring system 1 for monitoring corrosion in an environment such as a pipeline 9, is shown in FIG. 1. The corrosion monitoring system 1 generally comprises a sensor assembly 3 comprising a housing 21 for a reference element 31 and an exposed element 51, electronic circuitry 5 and a cable 7 for connecting the electronic circuitry to the sensor assembly 3.

The exposed element and the reference element are electrically connected in series and connected to a current generator 11,15 which drives current through the series circuit. The elements are connected to the electronic circuitry at pick-off points, e.g. points 33,35,53,55. The points define two portions on each of the sensor elements for the current to flow through. The electronic circuitry further comprises voltage monitoring means 11,19 arranged to monitor the voltage developed across each of the regions defined by the points of the exposed and reference elements.

The electronic circuitry further includes a current multiplexer 13 for alternately switching the current supplied to different points on the exposed and reference elements, and a voltage monitoring multiplexer 17 for switching the serial link electrically connecting the elements, and also for the voltage monitoring means to measure alternately the voltage across each element.

Each of the elements 31,51 of the sensor arrangement 3 have a closed-ring configuration. The reference closed-ring element 31 is electrically connected in series with the exposed closed-ring element 51. Conveniently, the sensor in any of the embodiments may be constructed to fit any pipeline that is to be monitored for corrosion/erosion. The exposed element and the reference element may be formed from adjacent sections or slices of the pipeline. This construction of the sensor elements ensures that the sensor elements are near to identical as possible including the material coefficient of resistivities. The process by which the slices are formed is preferably a process that minimises change to the microstructure of the material both local to and remote from the edges of the elements, and may for example include spark machining, wire corrosion, etching and the like. Each section or slice of the pipeline is preferably in the range of 8-12 mm wide. The thickness of the elements 31,51 are determined by the dimensions of the pipeline.

Figure 2:
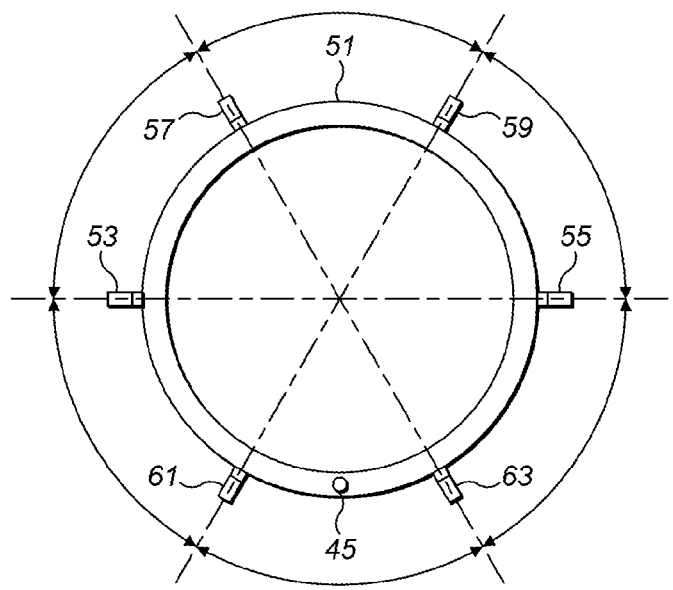
FIG. 2 shows a cross-sectional view of an exposed element of the corrosion sensor of U.S. Pat. No. 6,946,855.
Figure 3:
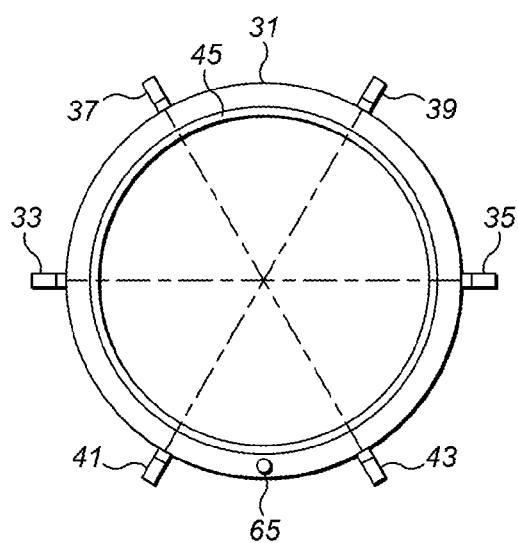
FIG. 3 shows a cross-sectional view of a reference element of the corrosion sensor of U.S. Pat. No. 6,946,855.

The elements maintain the radial orientation when mounted in the sensor. As shown in FIGS. 2 and 3, orientation marks 45,65 are provided on the elements which are aligned when mounted in the sensor 3. The orientation marks are made prior to parting of the elements from the pipeline material. The elements 31,51 are co-axially spaced and separated by a spacer ring 71. The spacer ring is coated with an insulating material such as epoxy resin or ceramic or the like. The material of spacer ring may form part of the housing 21 and the material of the spacer ring may also insulate the elements 31,51 from the pipeline when the sensor is mounted in the pipeline 9.

Each ring element 31,51 consists of additional co-planer pick-off points equally spaced around the outer circumference of the ring. The pick-off points are formed typically by spot welding, i.e. localised heat treatment to minimise any disturbance to the resistive properties of the elements. For example, each ring comprises four such points in addition to points 33,35,53,55 as discussed above for connecting the sensor elements to the electronic circuitry 5.

The pick-off points define three regions on each portion of each element. On the reference ring element 31 pick-off points 37,39 define three sectors on the upper portion of the reference element and pick-off points 41,43 define three sections on the lower portion of the reference element. Similarly, on the exposed ring element 51 pick-off points 57,59 define three sections on the upper portion of the exposed element and pick-off points 61,63 define three sectors on the lower portion of the exposed element.

Figure 4:
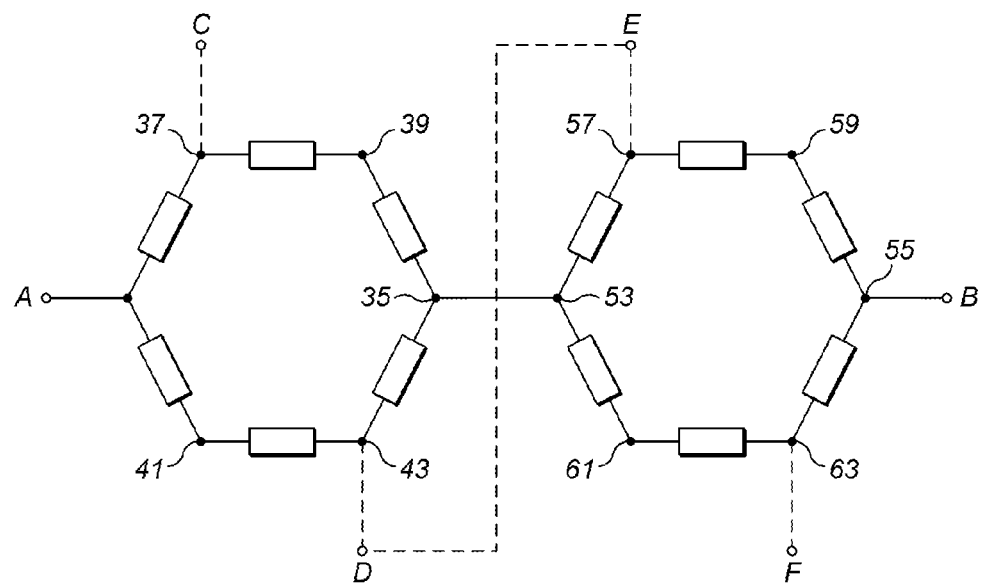
FIG. 4 shows a block diagram of the electrical connection point configuration of the reference element and exposed element of the corrosion sensor of U.S. Pat. No. 6,946,855.

Referring to FIG. 4, a current input $I_{in1}$ is shown at a position A at pick-off point 33 of the reference ring element 31 and a current output $I_{out1}$ is shown at position B at pick-off point 55 of the reference ring element 51. In this arrangement, the elements are electrically connected at points 35 and 53 via multiplexer 17 for example, and position A and B of the elements are electrically connected to the current multiplexer 13.

A second current input $I_{in2}$ is shown at a position C at point 37 and a second current output $I_{out2}$ is shown at a position D at point 43 of the reference ring element. Similarly, a third current input $I_{in3}$ is shown at a position E at point 57 and a third current output $I_{out3}$ is shown at a position F at point 43 of the exposed ring element. In this arrangement, the ring elements are electrically connected as shown at position D and E from points 43 and 57 via multiplexer 17 for example, and the position C and B are electrically connected to the current multiplexer 13.

In this configuration, the current multiplexer 13 allows for selectively and alternately switching the current supplied to the different points A-B or C-F and simultaneously the multiplexer 17 for example may switch the linking points 35-53 or 43-57, respectively, on the exposed and reference elements and provides for a selectable dual position current generator which drives the current through the series circuit. The second current input position C is adjacent to a sector pick-off position A.

Similarly, each of points 33,37,39,35,41,47 of the reference element and each of points 53,57,59,55,63,61 of the exposed element may be connected to the voltage monitoring multiplexer 17 for switching the voltage monitoring means to measure alternately the voltage across each sector defined by the points. The multiplexer is provided for switching the voltage monitoring positions across each ring and the voltages for each sector.

With reference to FIGS. 1 and 4, the operation of the sensor generally involves measuring the voltages across each sector on each of the elements, switching the drive current position and measuring the voltages with the new drive current position. In this configuration, there are six sectors on each ring. The resistance ratio of each sector is determined from the voltages developed across each sector. For the exposed element $R_s$, sector Ra is defined by points 53,57 which is indicated as 0°-60°, sector Rb is defined by points 57,59 which is indicated as 60°-120°, Rc is defined by points 59,55 which is indicated as 120°-180°, Rd is defined by points 55,63 which is indicated as 180°-240°, Re is defined by points 63,61 which is indicated as 240°-300°, and Rf is defined by points 61,53 which is indicated as 300°-360° of the exposed ring element. Sectors of the reference element are similarly identified, where sector $R_r$a is defined by points 33,37 indicated as 0°-60°, sector $R_r$b is defined by points 37,39 indicated as 60°-120°, $R_r$c is defined by points 39,35 indicated as 120°-180°, $R_r$d is defined by points 35,43 indicated as 180°-240°, $R_r$e is defined by points 43,41 indicated as 240°-300°, and $R_r$f is defined by points 41,33 indicated as 240°-300° of the reference ring element.

The ratio of resistance of the elements $R_s/R_r$ is first determined and the exposed element ratios Ra/Rb, Ra/Rc, Rf/Rd, Rf/Re are measured along with the reference element ratios $R_r$a/$R_r$b, $R_r$a/$R_r$c, $R_r$f/$R_r$d, $R_r$f/$R_r$e.

In this configuration the current multiplexer 13 then switches the drive current position switch to current input position C and current output position F. At this time, the points electrically linking the elements serially, are switched by multiplexer 17 for example from points 35,53 to points 43,57, as shown by a dashed line in FIG. 1, D-E. In this arrangement, the current input, current output, and the electrical connection between the elements rotates by 60 degrees.

The resistance ratios Ra/Rf and $R_r$a/$R_r$f are then measured. Both the element $R_r$,$R_s$ profiles may then be derived and profile in terms of Ra/Ra, Ra/Rb, Ra/Rc, Ra/Rd, Ra/Re and Ra/Rf, and $R_r$a/$R_r$a, $R_r$a/$R_r$b, $R_r$a/$R_r$c, $R_r$a/$R_r$d, $R_r$a/$R_r$e and $R_r$a/$R_r$f, respectively. Then, the $R_s$ profile is modified from the $R_r$ profile by the equation:

$$Ra/Rb = (T-xb)/(T-xa) \quad (1)$$

where T=ring thickness, xa=metal loss in sector a, and x1+x2=2T(1−1/($R_s/R_r$)), where x1=effective metal loss of upper section of the ring element, x2=effective metal loss of lower section of the ring element. Similarly, the metal loss in each other sector may be determined. A pressure sensor 73 may be positioned through an access hole in the spacer ring. The spacer ring 71 may also provide access for other monitoring devices such as electrochemical noise and linear polarisation resistance devices, and the like. For example, under typical load conditions, the pressure may be measured using the pressure sensor. Conveniently, the pressure readings, for example, may be used to calculate and eliminate changes caused by hydrostatic pressure effects.

The Present Invention

The present invention relates to an apparatus and method for monitoring a conductive fluid conduit arranged to carry a fluid stream. The conductive fluid conduit has one surface exposed to the fluid stream and another surface protected from the fluid stream. The present invention is intended to non-intrusively monitor the pipe wall thickness of an oil or gas conduit. It is envisaged that the present invention would be particularly suitable for monitoring oil or gas export pipelines which are used to export oil or gas away from the manifold of an oil or gas well.

Figure 5:
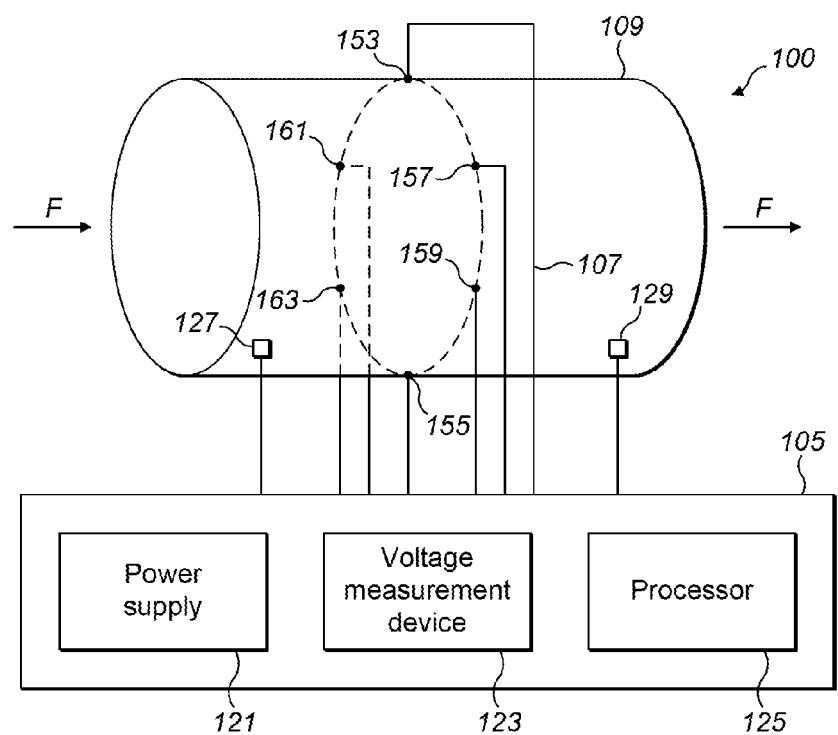
FIG. 5 schematically illustrates an apparatus for monitoring a conductive pipe in accordance with one embodiment of the present invention.

FIG. 5 schematically shows an apparatus 100 in accordance with the present invention. The apparatus 100 in FIG. 5 is being used to monitor the wall thickness of a conductive pipe 109. It is expected that the wall thickness will change over time due to corrosion and/or erosion of an inner surface of the pipe due to fluid flowing through the pipe.

The apparatus includes electrical contact points (or pick-off points) 153,157,159,155,163,161 connected to an outer surface of the pipe 109. The contact points 153,157,159, 155,163,161 are coplanar in a plane perpendicular to a flow direction F of fluid through the pipe. In other words, the contact points 153,157,159,155,163,161 are coplanar in a plane perpendicular to a longitudinal axis of the pipe 109. Furthermore, the contact points 153,157,159,155,163,161 are equally spaced around an outer circumference of the pipe 109. Thus, the contact points include three pairs of diametrically opposed electrical contact points 153 & 155, 157 & 163, and 159 & 161. It will be appreciated that alternative configurations of contact points may be used within the scope of the present invention. For example, it would be possible to include additional or fewer contact points depending on the granularity of measurements required. In addition, it would be possible to dispose contact points at irregular intervals around the circumference of the pipe 109 so as to detect local defects. For example, the contact points could be primarily connected to a semi-circular half of the pipe such that the monitoring could concentrate on either the bottom half or the top half of the pipe.

The apparatus also includes electronic circuitry 105 corresponding to the circuitry 5 of the corrosion sensor described in U.S. Pat. No. 6,946,855. Cabling 107 connects the circuitry 105 to the contact points 153,157,159,155,163, 161. The circuitry 105 includes a power supply 121, a voltage measurement device 123, and a processor 125. The power supply 125 is connected to the external (i.e. non-exposed or protected) surface of the pipe 109.

The apparatus also includes an acoustic sensor 127. The acoustic sensor 127 may be an external passive acoustic transducer. The acoustic sensor 127 is acoustically coupled to the pipe 109. The acoustic sensor is arranged to provide a signal which varies in dependence upon acoustic noise generated by impacts of particles and fluid in the fluid stream on an inner (exposed) surface of the pipe 109. Signals from the acoustic sensor 127 are received by the electronic circuitry 105 and processed by the processor 125.

The apparatus may also include additional sensors 129, such as a temperature sensor and/or a pressure sensor. For example, pressure may be measured externally using strain or fibre sensors (e.g. pressure may be measured by detecting axial and longitudinal strain on the external surface of the pipe 109). Signals from the additional sensors 129 are received by the electronic circuitry 105 and processed by the processor 125.

In use, the operation of the apparatus 100 generally involves measuring the voltages across each sector of the apparatus 100, switching the drive current position and measuring the voltages with the new drive current position. The resistance ratio of each sector is determined from the voltages developed across each sector.

The power supply 121 is used to drive an external current injection into the outer surface of the conductive pipe 109 using a selected pair of current input/output points. In a preferred embodiment, the current input/output points are chosen from the external contact points 153,157,159,155, 163,161. Two current injection modes are used so as to resolve the current split. In each current injection mode, the power supply 121 is connected to the pipe 109 by means of a different pair of current input/output points.

Figure 6:
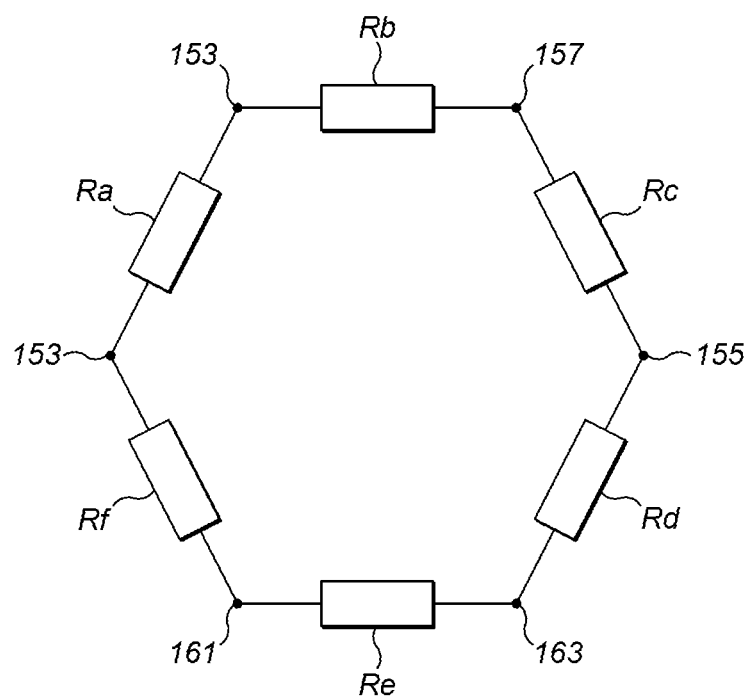
FIG. 6 shows a block diagram of the electrical connection point configuration of the apparatus of FIG. 5.

For example, in the first current injection mode, the current may be injected via the contact point 153 and travel through the conductive pipe 109 to flow out at the contact point 155. The voltage measurement device 123 is used to measure the voltage between pairs of contact points 153, 157,159,155,163,161. For this purpose, the voltage measurement device 123 may include a voltage monitoring multiplexer (similar to voltage monitoring multiplexer 17) for switching the voltage measurement device 123 to measure alternately the voltage across each sector defined by the contact points. The processor 125 is then used to calculate the resistance of the current path between the various pairs of contact points. In particular, the ratios of resistance Ra/Rb, Ra/Rc, Rf/Rd and Rf/Re are measured (see FIG. 6) using a high frequency AC current injection in the reference mode, and using a DC or low frequency AC current injection in the sample mode. Thus, for one current injection, multiple voltage measurements are taken. This methodology makes the most of each current injection, which is particularly beneficial since energy is scarce along an export pipeline.

It should be noted that the injected current will take the path of least resistance between the input and output current injection contact points 153 & 155. Therefore, the injected current will tend to take the shortest path available through the conductive pipe 109. In the case of FIG. 1, this means that the highest current density will be along a circumferential path coplanar with the electrical contact points 153, 157,159,155,163,161. However, the current density will not be entirely constrained to the narrow circumferential line which represents the shortest path through the conductive pipe 109. Instead, the current density will be more spread out to encompass a narrow longitudinal section of the pipe 109. Thus, the present apparatus effectively creates a virtual "ring" over which electrical resistance is measured, as compared to the corrosion sensor of U.S. Pat. No. 6,946,855 which uses two real "ring" elements (the reference element 31 and the sample element 51). The virtual measurement "ring" includes a narrow longitudinal section of the pipe 109, and thus the present apparatus provides electrical resistance measurements over an extended (rather than constrained) straight or curved section of the pipe 109. Electromagnetic modelling software may be used to model the predicted current density so as to ascertain the expected longitudinal extent of the virtual measurement "ring" and so as to optimise the spacing between virtual rings in the case where a plurality of separate, longitudinally spaced apparatuses 100 are used. It should be noted, however, that it is not intended to move current longitudinally along the pipeline on average.

In the second current injection mode, the current may be injected via the contact point 157 and travel through the conductive pipe 109 to flow out at the contact point 163. The voltage measurement device 123 is again used to measure the voltage between pairs of contact points 153,157,159, 155,163,161. The processor 125 is then used to calculate the resistance of the current path between the various pairs of contact points. In particular, the ratio of resistance Ra/Rf is measured (see FIG. 6) using a high frequency AC current injection in the reference mode, and using a DC or low frequency AC current injection in the sample mode. Both the reference and sample resistance profiles of the pipe 109 may then be derived, and the sample resistance profile may be modified with the reference resistance profile using methodology similar to that of Equation (1). The second current injection is therefore used to resolve the current split over the two halves of the pipe defined by the first current injection.

In a sample mode of operation of the apparatus 100, the injection current is chosen such that it is able to penetrate through the full thickness of the pipe wall. For example, a low frequency AC current could be used. Alternatively a DC current could be used. Thus, the calculated resistance provides an indication of the thickness of the pipe wall. In particular, a thicker pipe wall will have a lower resistance than a thinner pipe wall which has been eroded/corroded by fluid flow through the pipe 109.

Electrical resistance/resistivity is known to vary with temperature. Therefore, the resistance calculated by the processor 125 in the sample mode of operation of the apparatus will be dependent not only on the thickness of the pipe wall thickness, but also on temperature. Thus, the apparatus has an alternative mode of operation (the reference mode of operation) in which a comparative resistance measurement may be made independently of the thickness of the pipe wall. This reference resistance measurement allows the sample resistance measurement to be modified to compensate for temperature dependence effects. Thus, the processor 125 may be used to determine the thickness of the pipe wall based on the modified sample values of electrical resistance. Consequently, the processor may be used to determine the corrosion and/or erosion of the inner pipe wall based on the modified sample values of electrical resistance.

In the reference mode of operation of the apparatus, the injection current is chosen to be a high frequency alternating electric current (AC) such that the current does not penetrate through the full thickness of the pipe wall due to the "skin effect". The skin effect describes the tendency of an alternating electric current to distribute itself within a conductor with the current density being largest near the surface of the conductor, and decreasing at greater depths. Specifically, the AC current density J in a conductor decreases exponentially from its value at the surface $J_s$ according to the depth d from the surface, as follows:

$$J = J_s e^{-d/\delta}$$

where $\delta$ is called the skin depth. The skin depth is thus defined as the depth below the surface of the conductor at which the current density has fallen to 1/e (about 0.37) of $J_S$. For conductors, the skin depth is well approximated as:

$$\delta = \sqrt{\frac{2\rho}{\omega\mu}}$$

where $\rho$ is the resistivity of the conductor, $\omega$ is the angular frequency of current (i.e. $\omega=2\pi\times$frequency), and $\mu$ is the absolute magnetic permeability of the conductor.

Referring to the embodiment of FIG. 5, in the reference mode of operation, the skin effect causes the high frequency alternating drive current to flow mainly in the "skin" of the conductive pipe 109. Specifically, the electric current flows near the inner and outer surfaces of the pipe 109. Thus, the total thickness of the pipe wall becomes irrelevant at high frequency because the current cannot utilise the full pipe thickness at high frequencies. Hence, in the reference mode of operation it is possible to make a measurement of resistance of the pipe that is independent of corrosion and/or erosion effects (i.e. reductions in pipe wall thickness due to metal loss). These reference measurements of resistance allow for temperature compensation of the corresponding sample measurements of electrical resistance in the sample mode of operation of the apparatus. In other words, the apparatus measures and compensates for temperature and pressure by creating a virtual circumferential "reference ring" by switching to high frequency AC to induce "skin effects" such that pipe wall thickness will not influence impedance measurements. The skin depth and temperature measurement may be tuned through calibration.

Measurements of temperature and pressure, etc. taken by the additional sensors 129 may also be used by the processor 125 to modify the sample resistance measurements if desired. Thus, it is possible to compensate for pressure variations. Temperature measurements taken by the sensors 129 provide redundancy in the temperature compensation measurements as well as providing an independent method of measuring temperature for diagnostic purposes.

In addition, acoustic measurements taken by the acoustic sensor 127 may be used by the processor 125 to estimate a quantity of particulate matter (e.g. sand) in the fluid stream. Qualitative sand measurement is performed based on acoustic measurements due to particle impacts over an extended surface of the pipe 109. Using the acoustic sensor 127 in combination with the electrical resistance measurements enables the apparatus to qualitatively monitor particulate matter in a fluid stream as well as the corrosive effects of that particulate matter, such as the erosion rate and the amount of erosion (i.e. the cumulative erosion damage). Furthermore, because the apparatus monitors corrosion and acoustic noise on the same target surface, this enables more accurate differentiation between liquid and solid impact events since the events may be analysed in terms of both their acoustic and corrosive signatures. The acoustic measurements may also be used to detect the passing of pigs within the pipe 109.

The power supply 121 is able to be switched between the reference and sample modes of operation to enable reference and sample measurements to be taken using the same pair of current input/output points. The circuitry 105 may include a current multiplexer (similar to the current multiplexer 13 of U.S. Pat. No. 6,946,855) for this purpose. The reference and sample measurements may be obtained successively (i.e. one after the other in sequence or in turn). Having made a multiple pairs of voltage measurements for a given current injection, the circuitry 105 enables the power supply 121 to supply electrical current to a different pair of current input/output points chosen from the contact points 153,157,159, 155,163,161 on the external surface of the pipe 109. Thus, as for corrosion sensor of U.S. Pat. No. 6,946,855, it is possible to build up a picture of the pipe wall thickness (and corrosion and/or erosion of the inner pipe wall) in different sectors of the pipe 109 that are defined by the locations of the contact points 153,157,159,155,163,161.

One advantage of the present invention is that the apparatus is inherently non-intrusive since the electrical contact points (electrodes) are connected to the outer surface of the pipe 109 itself without any need for access to the interior of the pipe 109. In contrast, the corrosion sensor of U.S. Pat. No. 6,946,855 uses reference and sample elements that are separate to the pipe itself. Furthermore, the sample element must be located inside the pipe such that it is exposed to the fluid flow, which makes the system intrusive.

Another advantage of the present invention is that there is no need for separate reference and sample elements (like reference element 31 and exposed element 51 of the corrosion sensor of U.S. Pat. No. 6,946,855) in order to compensate the sample measurements for temperature variations within the pipe 109. Instead, the same contact points 153, 157,159,155,163,161 are used for both the sample and reference measurements in the present apparatus.

In general, temperature does not tend to vary significantly along the longitudinal length of the oil or gas pipe 109. There may be some temperature variation radially around the pipe 109, but any radial temperature variations would be accounted for by the sector-based measurements using different pairs of contact points 153,157,159,155,163,161. In some situations (e.g. where insulation of the pipe is poor), there may additionally be a small temperature gradient through the wall of the pipe 109 between the inner and outer surfaces of the pipe. Such temperature gradients may also be monitored using the present apparatus. In particular, a high frequency AC current injection may initially be used to obtain a reference measurement of electrical resistance of the pipe 109 as described above. The frequency of the high frequency AC injected current may then be reduced slightly such that the skin depth increases and the reference electrical resistance measurement corresponds to a slightly larger skin depth of the pipe wall. Subsequent stepwise decreases in the frequency of the high frequency AC injected current may be used to monitor the electrical resistance of thicker and thicker sections of the outer pipe wall. Thus, it is possible to monitor variations in temperature with pipe wall depth.

Although preferred embodiments of the invention have been described, it is to be understood that these are by way of example only and that various modifications may be contemplated.

The present apparatus may also be used to monitor a curved section of an oil or gas pipe, rather than the straight pipe section shown in FIG. 5.

Multiple, longitudinally spaced apparatuses as described above could be used along a pipe to monitor changes lengthwise along the pipe.

In an alternative embodiment, it will be appreciated that the current input/output points could be distinct from the electrical contact (or pick-off) points if desired. However, it is preferred that current is injected via the electrical contact (or voltage pick-off) points.

The invention claimed is:

1. Apparatus for monitoring a conductive fluid conduit arranged to carry a fluid stream, the apparatus comprising:
    a power supply having a reference mode of operation and a sample mode of operation, wherein in the reference mode of operation the power supply is operable to supply an alternating electric current through the fluid conduit at a high frequency such that the current is confined near the surface of the fluid conduit due to the skin effect, and wherein in the sample mode of operation the power supply is operable to supply an electric current through a full thickness of the fluid conduit;
    a plurality of electrical contact points connected to the fluid conduit;
    a voltage measurement device operable to measure the voltage between pairs of said electrical contact points so as to obtain reference values of electrical resistance of the fluid conduit when the power supply is in the reference mode of operation and so as to obtain sample values of electrical resistance of the fluid conduit when the power supply is in the sample mode of operation; and
    a processor operable to modify the sample values of electrical resistance based on the corresponding reference values of electrical resistance so as to compensate for temperature variations.

2. The apparatus of claim 1 wherein the processor is further operable to determine a thickness of the fluid conduit based on the modified sample values of electrical resistance.

3. The apparatus of claim 1 wherein in the sample mode of operation the power supply is operable to supply an alternating electric current at a low frequency through a full thickness of the fluid conduit.

4. The apparatus of claim 1 wherein in the sample mode of operation the power supply is operable to supply a direct electric current through a full thickness of the fluid conduit.

5. The apparatus of claim 1 wherein the apparatus has a plurality of current injection modes, and wherein in each current injection mode the power supply is operable to be connected to the fluid conduit by means of a respective pair of current input/output points.

6. The apparatus of claim 5 wherein the pairs of current input/output points are selected from the plurality of electrical contact points.

7. The apparatus of claim 1 further comprising an acoustic sensor that is acoustically coupled to the fluid conduit, wherein the acoustic sensor is arranged to provide a signal which varies in dependence upon acoustic noise generated by impacts of particles and fluid in the fluid stream on the fluid conduit.

8. The apparatus of claim 7 wherein the processor is further operable to qualitatively indicate an amount of particulate matter in the fluid stream based on the signal provided by the acoustic sensor.

9. The apparatus of claim 1 wherein the processor is further operable to determine the corrosion and/or erosion of the fluid conduit based on the modified sample values of electrical resistance.

10. The apparatus of claim 1 further comprising a pressure sensor adapted to sense a pressure associated with the fluid stress.

11. The apparatus of claim 10 wherein the processor is further operable to modify the sample values of electrical resistance based on the sensed pressure so as to compensate for pressure variations.

12. The apparatus of claim 1 wherein the electrical contact points are disposed in a plane perpendicular to a flow direction of the fluid stream along the fluid conduit.

13. A system comprising a plurality of apparatuses for monitoring a conductive fluid conduit arranged to carry a fluid stream, the plurality of apparatuses being mutually spaced along the fluid conduit in the flow direction, each of the plurality of apparatuses comprising:
    a power supply having a reference mode of operation and a sample mode of operation, wherein in the reference mode of operation the power supply is operable to supply an alternating electric current through the fluid conduit at a high frequency such that the current is confined near the surface of the fluid conduit due to the skin effect, and wherein in the sample mode of operation the power supply is operable to supply an electric current through a full thickness of the fluid conduit;
    a plurality of electrical contact points connected to the fluid conduit;
    a voltage measurement device operable to measure the voltage between pairs of said electrical contact points so as to obtain reference values of electrical resistance of the fluid conduit when the power supply is in the reference mode of operation and so as to obtain sample values of electrical resistance of the fluid conduit when the power supply is in the sample mode of operation; and a processor operable to modify the sample values of electrical resistance based on the corresponding reference values of electrical resistance so as to compensate for temperature variations.

14. A method for monitoring a conductive fluid conduit arranged to carry a fluid stream, the method comprising the steps of:
   obtaining reference values of electrical resistance of the fluid conduit by driving an alternating electric current through the fluid conduit at a high frequency such that the current is confined near the surface of the fluid conduit due to the skin effect, and by measuring the voltage between pairs of electrical contact points connected to the fluid conduit;
   obtaining sample values of electrical resistance of the fluid conduit by driving an electric current through a full thickness of the fluid conduit, and by measuring the voltage between said pairs of electrical contact points; and
   modifying the sample values of electrical resistance based on the corresponding reference values of electrical resistance so as to compensate for temperature variations.

15. The method of claim 14 further comprising determining a thickness of the fluid conduit based on the modified sample values of electrical resistance.

16. The method of claim 14 wherein the step of obtaining sample values of electrical resistance comprises driving an alternating electric current at a low frequency through a full thickness of the fluid conduit.

17. The method of claim 14 wherein the step of obtaining sample values of electrical resistance comprises driving a direct electric current through a full thickness of the fluid conduit.

18. The method of claim 14 wherein a measurement cycle comprises the steps of obtaining reference values of electrical resistance and obtaining sample values of electrical resistance for a plurality of current injection modes, wherein in each current injection mode electric current is driven through the fluid conduit via a respective pair of current input/output points.

19. The method of claim 18 wherein the pairs of current input/output points are selected from the pairs of electrical contact points.

20. The method of claim 14 wherein the steps of obtaining reference values of electrical resistance and obtaining sample values of electrical resistance are performed successively.

21. The method of any of claim 14 wherein the step of obtaining reference values of electrical resistance further comprises driving an alternating electric current through the fluid conduit at at least one other high frequency, and measuring the voltage between said pairs of electrical contact points such that a temperature gradient through the thickness of the fluid conduit may be determined.

* * * * *